United States Patent [19]
Kreischer et al.

[11] Patent Number: 6,017,598
[45] Date of Patent: *Jan. 25, 2000

[54] MULTILAYER POLYMER FILM FOR A MULTICHAMBER MEDICAL BAG AND PROCESS FOR FABRICATION THEREOF

[75] Inventors: Thomas Kreischer, Saarbrucken; Klaus Heilmann, St. Wendel; Thomas Nicola, Forbach; Michael Zimmermann, St. Wendel, all of Germany

[73] Assignee: Fresenius AG, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/564,134
[22] PCT Filed: Mar. 28, 1995
[86] PCT No.: PCT/EP95/01152
  § 371 Date: May 28, 1996
  § 102(e) Date: May 28, 1996
[87] PCT Pub. No.: WO95/26177
  PCT Pub. Date: Oct. 5, 1995

[30] Foreign Application Priority Data

Mar. 29, 1994 [DE] Germany .............................. 44 10 876

[51] Int. Cl.⁷ .................................. A61J 1/10; B32B 7/06
[52] U.S. Cl. ....................... 428/35.4; 428/35.2; 428/35.7; 428/36.6; 428/43; 428/500; 428/516; 604/410; 604/416; 206/219; 206/828; 383/38; 383/200; 383/207; 156/306.3

[58] Field of Search .................................. 428/35.7, 36.6, 428/43, 519, 35.2, 57, 500, 516, 35.4; 604/410, 416; 206/219, 828; 383/38, 200, 207; 156/306.3

[56] References Cited

U.S. PATENT DOCUMENTS

| | | |
|---|---|---|
| 4,210,686 | 7/1980 | Gajewski et al. ....................... 428/35.2 |
| 4,496,046 | 1/1985 | Stone et al. . |
| 4,778,697 | 10/1988 | Genske et al. .......................... 428/35.2 |

FOREIGN PATENT DOCUMENTS

| | | |
|---|---|---|
| 90104603 | 11/1986 | European Pat. Off. . |
| 89110379 | 6/1989 | European Pat. Off. . |
| 90125765 | 12/1990 | European Pat. Off. . |
| 91918598 | 10/1991 | European Pat. Off. . |
| 94905826 | 2/1994 | European Pat. Off. . |
| 94103170 | 3/1994 | European Pat. Off. . |
| PCT/US93/02016 | 3/1993 | WIPO . |

*Primary Examiner*—Fred Teskin
*Attorney, Agent, or Firm*—Fulbright & Jaworski L.L.P.

[57] ABSTRACT

The invention concerns a multilayer polymer film and a multichamber bag, whose bag chambers are formed by seams in the outer border zone and by at least one seam in the chamber separation zone, whereby the seams are formed from the polymer materials facing the chambers. The polymer materials facing the chambers are inseparably sealed together in the outer border zone and sealed together in the chamber separation zone such that the seam is separable with a force which lies in the range from 5 to 20 N. The different strength of the bond from the sealing process is obtained by varying sealing temperatures.

14 Claims, 4 Drawing Sheets

MULTILAYER POLYMER FILM FOR A MULTICHAMBER MEDICAL BAG AND PROCESS FOR FABRICATION THEREOF

The invention concerns a multilayer polymer film for a multichamber medical bag for preparation of mixed medical solutions, which has at least two chambers which are separated from each other by a sealed separation zone to be opened and are sealed in the outer border zone, whereby in the seam of the outer border zone at least one tube is provided in at least one chamber.

Multichamber medical bags have been used for years for preparation of mixed solutions. The known multichamber bags have different systems as separation arrangements between the chambers.

One of these systems uses breakable separation parts made of rigid, breakable materials. These have the advantage of largely universal applicability, but have disadvantages to the extent that they only free a limited breaking or mixing opening and undesirable particle formation may occur upon breakage of the separation arrangement.

Such a system, which has a predetermined breaking point in the chamber separation zone, which can be broken, for example, by exerting pressure on one chamber, is disclosed in EP 0 378 183, whereby a peel strip is also advantageously included in the seal in the zone of the predetermined breaking point.

A second type of separation arrangement is designed as a squeezing system, which presses the films of the bag, for example, by means of external clamps for sealing and can be opened before use. The advantages of such squeezing systems lie in the possible large mixing opening which can as a rule be produced without any particles. However, such systems are disadvantageous to the extent that they are limited to film materials for the bags which must have high elasticity and temperature resistance in order to effect the desired separation. Often, such systems have leaks. In order to avoid these, it is necessary to precisely coordinate the tolerances of bag thickness and the squeezing system to each other.

In order not to be restricted in squeezing systems to certain types of films as materials for the multichamber bag and to improve the separation action, according to German patent DE 41 07 223, an elastic strip of film which serves as a seal during activation of the squeezing device is disposed is the region of the later mixing opening. Because of the squeezing arrangement and the strip of film, this system has the disadvantage that it is very expensive.

Consequently, the object of the invention is to make available another film for a multichamber medical bag which, upon sealing at a first low temperature, produces a peelable seam and, upon sealing at a second temperature, produces a durable seam.

This object is achieved according to the invention in that the layer of the multilayer film facing the chambers has essentially two components, i.e., a matrix polymer and a phase polymer. The surprising advantage of the multichamber bag made from the film according to the invention lies in the fact that it is possible, because of the polymer material facing the chambers, to form both inseparable seams in the outer border zone and subsequently separable seams in the chamber separation zone.

A seam in the chamber separation zone should be separable with a force in the range from 5 to 20 N. If the seam is separable with a force of less than 5 N, no reliable separation of the chambers is possible, since the bond can release by itself, for example, as a result of slight shocks during transport which exert pressure on one or a plurality of chambers. At a force of 20 N, the seam is can be separated only with great difficulty. There is the danger that instead of the seam, the film will tear and the bag will thus become leaky.

Moreover, the separation force of the seam must be high enough that the bag can withstand a drop from a two-meter height.

The above-described multichamber bag made of the film according to the invention permits a very simple design since neither breakable separation parts nor squeezing arrangements are required. Also, no additional sealing and film materials are needed in the chamber separation zone.

Nevertheless, a reliable separation of the chambers is obtained, whereby the separation is easy to open and, in addition, it leaves the largest possible cross section free.

Preferably, so-called blown or tubular films are used to fabricate the multichamber bag. These may possibly be folded and merely have to be closed, i.e., sealed, on two sides of the outer border, i.e., at the two openings. However, the use of individual sheets of film, which, however, have to be sealed all the way around, is also conceivable.

Generally, a multilayer film is used as a polymer material for multichamber bags. In a preferred embodiment, the multilayer film is a co-extruded multilayer film. It is further preferred that the multilayer film have two to seven layers. But a monofilm of a polymer material is also conceivable for the multichamber bag.

The materials of the multilayer film are selected such that the bag is as transparent and flexible as possible, but, in particular is heat sterilizable and biocompatible. For reasons of biocompatibility and from an environmental standpoint, the use of PVC, which always has a certain proportion of softeners, is ruled out, at least in the inner layer. For the same reasons, materials such as adhesion promoters, which could diffuse into the interior of the bag, should be ruled out.

For specific applications it is moreover necessary that the multilayer film have a gas barrier for oxygen and carbon dioxide as well as a water vapor barrier which prevents diffusion of these gases both into and out of the bag.

The layer of the multilayer film facing the chambers, hereinafter referred to as the inner layer, has essentially two components, i.e., a matrix polymer and a phase polymer. The system of matrix and phase polymers is referred to hereinafter as the matrix-phase polymer system.

Polymers with a high excitation or melting temperature range, such as polyethylene homopolymer, polyethylene copolymers, polypropylene homopolymer and polypropylene copolymer may be used as matrix polymers. Polyethylene is used as high density polyethylene (HDPE) or linear low density polyethylene (LLDPE). Of the matrix polymers mentioned, the polypropylene copolymer is preferred. Particularly preferred is a polypropylene random copolymer.

Polymers with a low excitation or melting temperature range, such as styrene ethylene/butylene styrene triblock polymer (SEBS), styrene ethylene/butylene styrene triblock polymer (SEBS) with a styrene ethylene/butylene diblock component (SEB), styrene ethylene/propylene styrene triblock polymer (SEPS), styrene butadiene styrene triblock polymer (SBS), and/or styrene isoprene styrene triblock polymer (SIS), as well as low density polyethylene (LDPE), linear low density polyethylene (LLDPE), terpolymers of ethylene, propylene, and a non conjugated diene (EPDM) and/or ethylene α-olefin copolymer may be used as phase polymers. Preferably, SEBS is used. The proportion of the phase polymer in the inner layer should be in the range from 1 to 40 wt.-%, based on the total matrix-phase polymer system.

The phase polymer may also have a processing aid. This aid is used to adjust the viscosity of the polymers. The amount of the aid should be in the range from 1 to 15 wt.-%, based on the amount of the phase polymer. Medical grade white oil may, for example, be used as a processing aid.

The seam of the outer border zone has at least one tube in at least one chamber, whereby this tube is a discharge tube. It is, however, also possible for this discharge tube to be a filling tube.

It is, however, preferred that, in addition to the discharge tube, each chamber to be filled also have a filling tube in the outer border zone. The filling tubes are, however, not absolutely necessary because it is also conceivable in the case of the two chamber bag to first seal the chamber separation zone and then fill each chamber and then seal the respective outer border zone.

It is also possible to isolate the discharge tube from the bag contents by forming an additional separable seam. This results in a three chamber bag which has two chambers to be filled, each with a filling tube, and an empty chamber with a discharge tube. It is possible thus to first mix the solutions of the two filled chambers and then to open the seam which isolates the discharge tube in order to thus release the bag contents. The advantage of this bag consists in that with it, it is possible to do without the disadvantageous break-off valve in the discharge tube.

In order that the chamber separation zone between the two filled chambers is opened first, it is possible to design the seam in the chamber separation zone between the two chambers to be filled such that the seam can first be opened at a specific point. This may be accomplished in that a part of the seam in the chamber separation zone between the two chamber to be filled is shaped, in a V, for example. In this case, the seam opens first at the point of the V since the force to be exerted is the least there. Consequently, the outer wall is preferably provided precisely in this region with a tear tab, preferably with two tear tabs.

Using these tear tab(s), it is then very simply possible, after complete mixing of the contents of the two filled chambers, to also open the part of the seam of the chamber separation zone which isolates the empty chamber which has the discharge tube.

In an additional separate embodiment, it is, of course, possible to use the seam which separates the discharge tube from the contents of the bag, even with bags which have only one chamber to be filled.

In another embodiment the multichamber bag has a suspension arrangement, which is designed preferably in the form of an opening in the sealed seam opposite the discharge tube. The suspension arrangement is, however, not restricted to this form.

The separable seal in the chamber separation zone can be separated by exerting pressure on at least one of the adjacent chambers, with the flat hand, for example. However, it is also possible to provide the outer wall in the chamber separation zone with a tear tab, preferably with two tear tabs.

The process for fabrication of the multichamber bag according to the invention is characterized in that the sealing is performed at a higher temperature in the outer border zone than in the chamber separation zone.

For this, it is necessary that the polymer material facing the chambers, preferably the inner layer of the multilayer film, have in its structure chain regions which require high (heat) energy input to excite vibration and a clearly lower [(heat) energy input] in other regions.

This structure results in the fact that with sealing at the low temperature only the zones fuse which require low energy to fuse. This is called partial fusing. In contrast, at the higher temperature, both the regions which require low energy input and the regions which require high energy input fuse. There is a more or less complete fusion of the inner layer. The sealing in the region of the low temperature yields a separable bond and an inseparable bond in the higher temperature areas.

For fabrication of a inner film layer with the above-described properties, in principle the following possibilities exist:

1. Polymer chains of high and low excitation or melting temperature are integrated into one polymer.
2. Both the matrix polymer and the phase polymer have chain areas with high and low excitation or melting temperature.
3. Polymers with high excitation or melting temperature form a matrix in which an additional polymer, which has chain areas with low excitation or melting temperature, is embedded. This so-called matrix-phase polymer system is preferred.

Sealing at the higher temperature is used in the outer border zone since this yields bonds which are no longer separable. This sealing in the outer border zone is preferably performed at a temperature in the range above 128° to 150° C.

Sealing at the low temperature is used in the chamber separation zone since it yields bonds which are separable. This sealing in the chamber separation zone is preferably performed at a temperature of $\leq 280°$ C.

The bottom temperature limit at which the sealing in the chamber separation zone can be performed in order to produce a separable seam varies depending on the inner layer film material used.

The duration of the sealing procedure is preferably in the range from 1 to 8 seconds, and the surface pressure exerted on the zones to be sealed during the sealing procedure is preferably in the range from 0.1 to 3 $N/mm^2$. However, for both parameters mentioned, values outside the ranges mentioned are also possible. Both parameters are thus not restricted to the preferred ranges.

The above-described multichamber bag made of the film according to the invention may be used for the preparation of mixed solutions, for example, for dialysis, infusion, or nutrition, whereby the term mixed solutions refers not only to a mixture of solutions, i.e., fluids, but also, for example, in the case of the two-chambered bag, to the mixing of a solution with a solid.

Additional details, characteristics, and advantages of the invention are presented in the following description of exemplary embodiments with reference to the drawings.

They depict.

Figure 1:
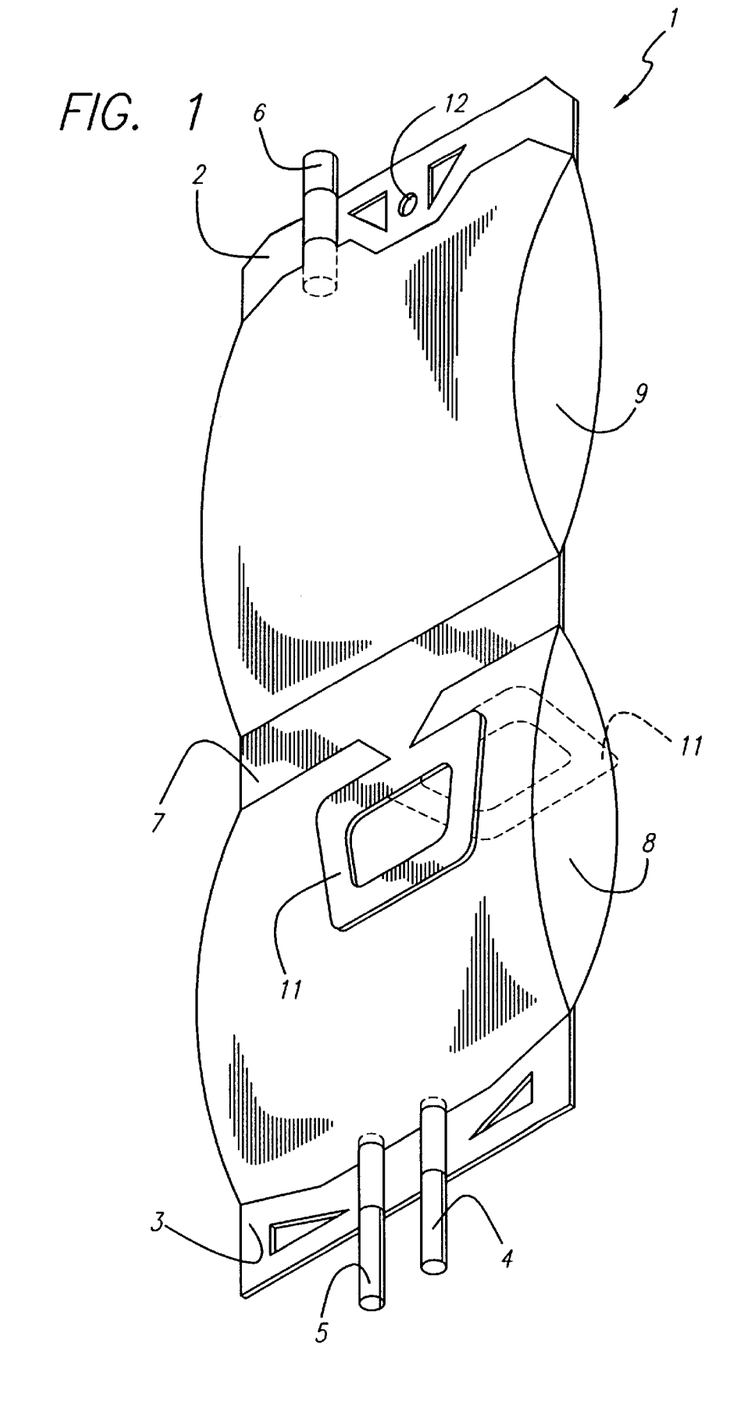
FIG. 1 a schematically simplified depiction of a preferred embodiment of a multichamber bag made of the film according to the invention.

FIG. 1 depicts a multichamber bag 1 according to a preferred embodiment of the present invention which is designed as a two-chamber bag with two bag chambers 8 and 9.

The bag 1 is formed from a folded blown film. The two chambers 8 and 9 are formed by seams 2 and 3 (so-called sealing bars) in the outer border zone and by the seam 7 in the chamber separation zone.

In each of the two seams in the outer border zone a tube 5, 6, which can be used for the filling of the bag chamber, is sealed in. In addition, the seam 3 in the outer border zone of the chamber 8 has an additional tube 4, which is designed as a discharge tube.

For easier handling, the seam 7 has on its outside two tear tabs 10.

Moreover, the seam 2, which is opposite the seam 3, which has the discharge tube, is outfitted with a suspension arrangement 11 in the form of an opening.

Figure 2:
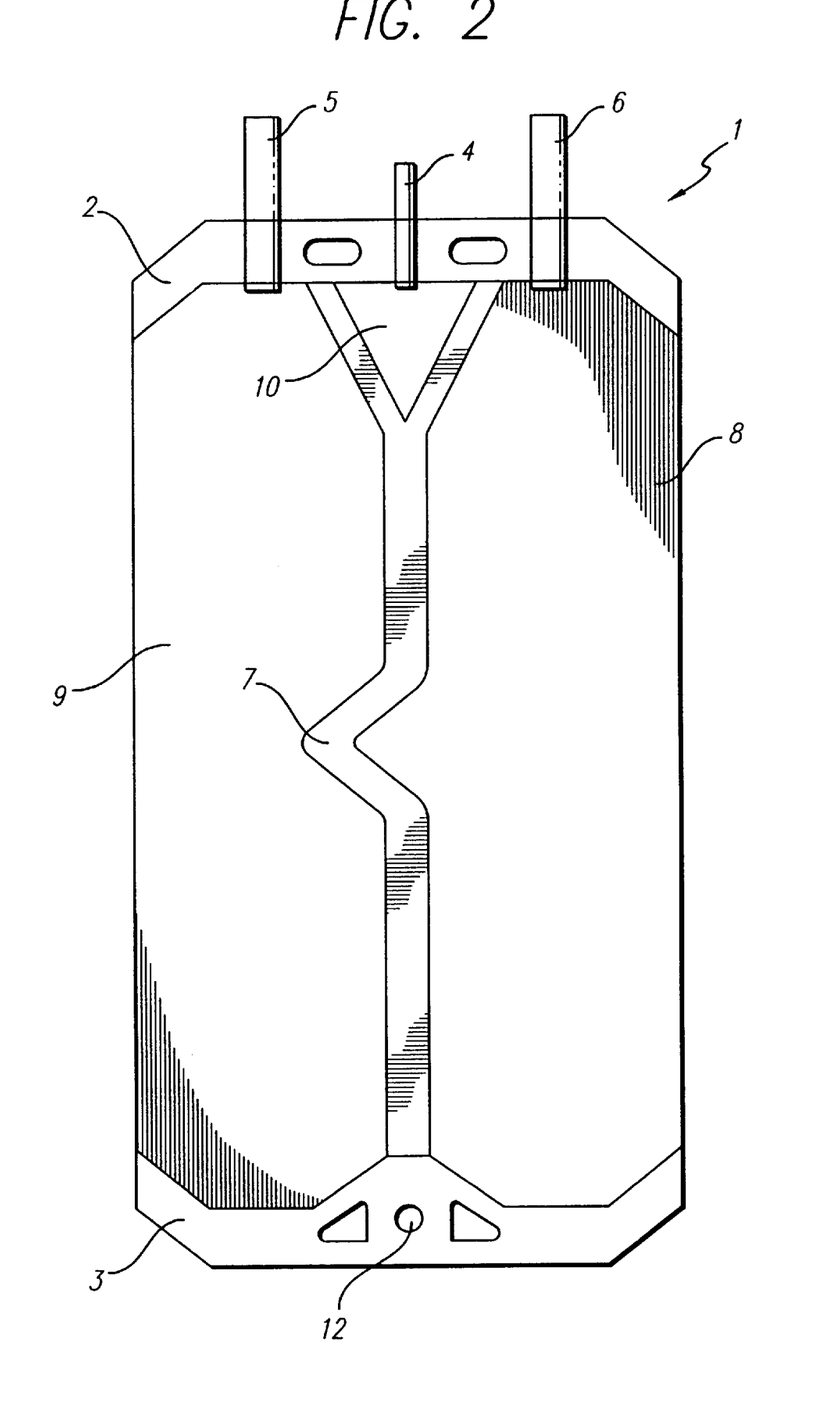
FIG. 2 a schematically simplified depiction of another preferred embodiment of a multichamber bag made of the film according to the invention.

FIG. 2 likewise depicts a multichamber bag 1 which is designed as a three-chamber bag, a preferred embodiment of the present invention.

The bag 1 is likewise formed from a folded blown film. The chambers 8, 9, and 10 are formed by seams 2 and 3 in the outer border zone and by a seam 7 in the chamber separation zone. The seam 7 in the chamber separation zone is designed such that, for one thing, it separates the two fillable chambers lengthwise of the blown film and, for another, it forms an empty chamber 10.

The two chambers 8 and 9 may be filled through filling tubes 5 and 6, which are sealed into the seam 2 of the outer border zone. In the same seam 2 of the outer border zone, the discharge tube 4, which is connected with the empty chamber 10, which is separated from the fillable chambers 8 and 9 by the seam 7, is also sealed in.

Moreover, a suspension arrangement 12 in the form of an opening is provided in the seam 3, which is opposite the seam 2, which has the discharge tube.

The present invention is, however, in no way restricted by the embodiments depicted in FIG. 1 and FIG. 2. Many other embodiments are conceivable.

The structure of the film is described in detail in the three following examples with reference to 3-layer films which represent a preferred embodiment. In the examples, the outer layer of the film, which is the side facing away from the chambered bag, is referred to as layer 1. Layer 2 is the middle film and layer 3 is the side of the film facing the chambers.

EXAMPLE 1
3-Layer Film Without Gas Barrier

The film is produced on a 3-layer co-extrusion blown film system. The extruders had 30 D length and are equipped with mixing and shearing parts. The co-extrusion tool is designed as a helical distributor tool.

| | Film structure: | | | |
|---|---|---|---|---|
| | Plastic type | Name | Manufacturer | MFI |
| Layer 1 | 100% PP homopolymer | Novolen 1302H | BASF | 1.8 (230/2.16) |
| Layer 2 | 70% VLDPE | Teamex 1000F | DSM | 3.0 (190/2.16) |
| | 30% PP homopolymer | Novolen 1302H | BASF | 1.8 (230/2.16) |
| Layer 3 | 70% PP random copolymer | Novolen 3200HX | BASF | 1.8 (230/2.16) |
| | 30% SEBS compound | 90% Kraton G1650 | Shell | |
| | | 10% Ondina G100 | Shell | |

The SEBS compound was previously compounded and granulated in a separate process step.

Ondina G100 is a paraffin-based medical-grade white oil.

EXAMPLE 2

Like Example 1, except that in Layer 3 a commercially available product of the company GW-Kraiburg was used as an SEBS compound.

| | Plastic type | Name | Manufacturer | MFI |
|---|---|---|---|---|
| Layer 3 | 70% PP-R | Novolen 3200HX | BASF | 1.8 (230/2.16) |
| | 30% SEBS compound | TF6AAF | GW-Kraiburg | |

The films are produced by co-extrusion. Depending on the film structure, starting materials and blends are combined in different layers. Besides the actual invention, the objective here is to obtain "separation seam" properties such as impact resistance, e.g., 2-m drop and gas barrier.

A 3-layer film which is structured according to Example 1 and 2 was subjected to a sealing test which is described in detail in the following. Two sealing bars with a length of 220 mm and a width of 10 to 15 mm were used as the sealing arrangement. The length of the sealing bars (220 mm) must be at least as long as, preferably somewhat longer than, the seam to be produced (180 mm). Four heating elements with a maximum power of 200 Watt each were applied per sealing bar at equal intervals and 25 mm below the sealing surface. Control was effected via a temperature sensor of the type PT 100 in the center between two heating elements. The film to be sealed was placed between the two sealing bars, one of which is stationary and the other movable. The movable sealing bar was pressed against the stationary sealing bar at a specified pressure by means of a piston (diameter 100 mm).

The sealing time was uniformly 6 seconds. The temperature was varied from 115° C. to 131° C., in steps of 2° C. It was possible to vary the pressure from 1 bar to 6 bar, in steps of 1 bar. Because of the geometry of the sealing arrangement (e.g., length and width of the sealing bars as well as the diameter of the piston) and the film (e.g., length and width of the seam), the various pressures yield values for the surface pressure on the zones to be sealed which fall in the range from 0.1 to 3 $N/mm^2$.

The starting temperature of the test sequence was set at 115° C., since the film presented no adhesion in the temperature range below that. At a sealing temperature of 131° C. and higher, the adhesion of the film surfaces is, on the other hand, so high that in the tensile strength tests the seam was inseparable and the film tore.

The seams of the multichamber bag sealed at different pressures and in the temperature range from 115° C. to 131° C. were subjected to a tensile strength test according to DIN 53457. The results of this tensile strength test are graphically presented in FIG. 3 and 4.

Figure 3:
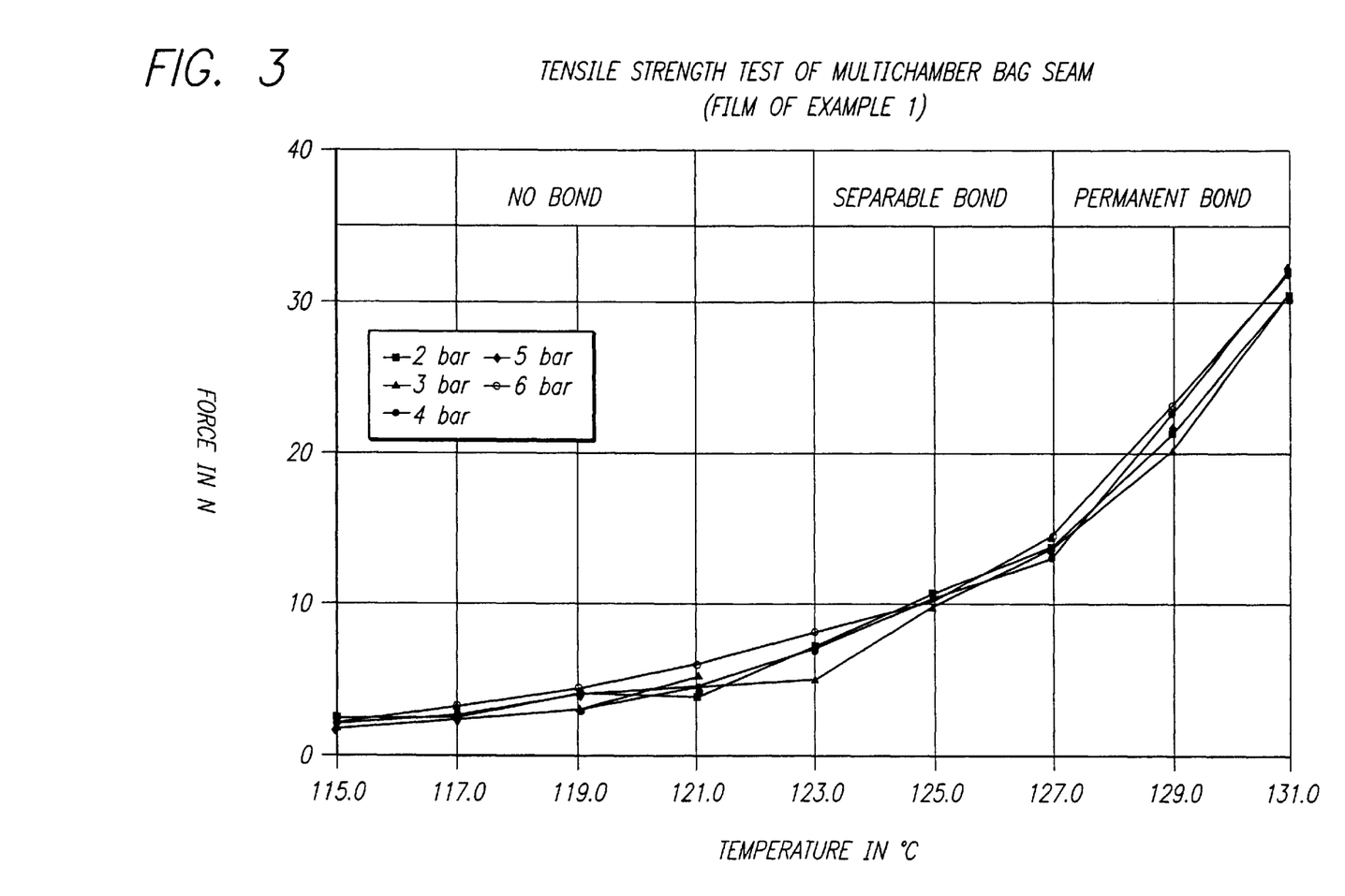
FIG. 3 graphically the results of the tensile strength test of a film according to Example 1.

As can be see in FIG. 3, for the films tested, which were produced according to Example 1, the following picture results:

In the temperature range from 115° C. to 122° C., the seam can be separated with a force which is less than 5 $N/mm^2$, i.e., the bond of the seal surface is too weak to be able to be used as a seam in multichamber bags according to the invention.

In the temperature range over 128° C. to 131° C., the seam can be separated only with a force of more than 20 $N/mm^2$, i.e., the seal surfaces are durably bonded to each other.

In the temperature range from 123° C. to 128° C., the seam can be separated with a force in the range from 5

N/mm² to 20 N/mm². Optimal peelability, i.e., a bond which can subsequently be separated, lies in this temperature range.

The pressure data are the pressures applied during sealing. The properties of the sealed seam are, however, essentially, independent of the pressure applied during sealing, as can readily be seen in FIG. 3.

For the film tested, the following temperature ranges result:

A seam which was sealed below 115° C. can be separated with a force of less than 5 N/mm², i.e., the bond of the sealing surface is too low to be able to be used as a seam in a multichamber bag according to the invention.

A seam which was sealed in the temperature range from 115° C. to 128° C. can be separated with a force in the range from 5 N/mm² to 20 N/mm², i.e., such a seam is used according to the invention in the chamber separation zone, since this bond can subsequently be separated.

A seam which was sealed in the temperature range above 128° C. can be separated only with a force of more than 20 N/mm², i.e., such a seam is used according to the invention in the outer border zone, since these sealing surfaces are durably bonded to each other.

Figure 4A:
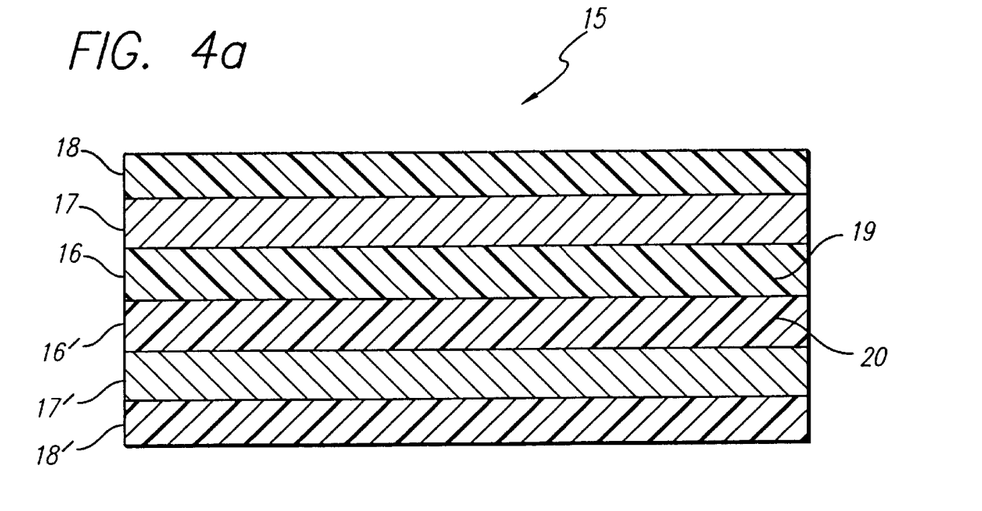
FIG. 4a the structure of a sealed multilayer film in the outer border zone, which is subsequently inseparable.

FIG. 4a depicts a 3-layer film structured according to Example 1 with inner layers 16 and 16' and with middle layers 17 and 17' as well as outer layers 18 and 18' which were sealed at a temperature higher than 128° C. The two inner layers 16 and 16', as can be seen in the graphic, are fused to each other such that an inseparable bond is formed.

Figure 4B:
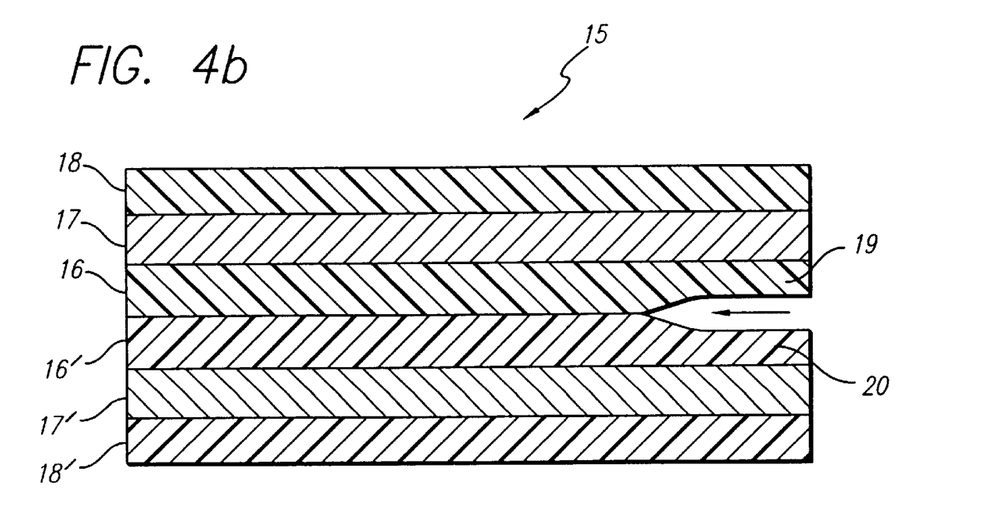
FIG. 4b the structure of a sealed multilayer film in the chamber separation zone, which is subsequently separable.

FIG. 4b depicts a 3-layer film structured according to Example 1, as was described in FIG. 4a. The difference from FIG. 4a consists only in that the film was sealed in the temperature range from 123° C. to 128° C. In this case, the two inner layers 16 and 16', as can be seen in the graphic, are fused to each other such that a subsequently separable bond is formed.

We claim:

1. A method of sealing a multilayer polymer film including two or more layers, which, at a first sealing temperature, forms a peelable bond and, at a second higher sealing temperature, forms a permanent bond, wherein the sealing layer has a matrix phase polymer system, wherein the matrix polymer is a polyethylene homopolymer, a polyethylene copolymer, a polypropylene homopolymer, or a polypropylene copolymer and the phase polymer is a styrene ethylene/butylene styrene triblock polymer with a styrene ethylene/butylene diblock component, a styrene ethylene/propylene styrene triblock polymer, a styrene butadiene styrene triblock polymer, and/or a styrene isoprene styrene triblock polymer, which method comprises forming a seam which can be separated by a force in the range of 5 to 20 N/mm² by sealing the film at a temperature in the range of from 123° C. to 128° C.

2. The method according to claim 1, characterized in that the multilayer film is a co-extruded multilayer film.

3. The method according to claim 1, characterized in that the multilayer film has two to seven layers.

4. The method according to claim 1, characterized in that the phase polymer contains a processing aid.

5. The method according to claim 1, characterized in that the proportion of the phase polymer is in the range from 1 to 40 wt. %, based on the matrix-phase polymer system.

6. The method according to claim 1, characterized in that the multilayer film has a gas barrier for oxygen and carbon dioxide as well as a water vapor barrier layer.

7. A multichamber medical bag (1) made of a polymer material for preparation of medical mixed solutions, which has at least two chambers (8 and 9), which are separated from each other by a sealed separation zone (7) to be opened and are sealed in an outer border zone (2, 3), whereby in the seam of the outer border zone at least one tube (4) is provided in at least one chamber, characterized in that it is fabricated from a multilayer polymer film including two or more layers, which, at a first sealing temperature, forms a peelable bond and, at a second higher sealing temperature, forms a permanent bond, wherein the sealing layer has a matrix phase polymer system, wherein the matrix polymer is a polyethylene homopolymer, a polyethylene copolymer, a polypropylene homopolymer, or a polypropylene copolymer and the phase polymer is a styrene ethylene/butylene styrene triblock polymer with a styrene ethylene/butylene diblock component, a styrene ethylene/propylene styrene triblock polymer, a styrene butadiene styrene triblock polymer, and/or a styrene isoprene styrene triblock polymer.

8. The multichamber bag according to claim 7, characterized in that the seam is separable in the separation zone (7) with a force which is in the range from 5 to 20 N/mm² and the seam in the outer border zone (2, 3) is inseparable.

9. The multichamber bag according to claim 7, characterized in that it is heat sterilizable.

10. The multichamber bag according to claim 7, characterized in that in addition to the discharge tube (4) each chamber to be filled also has at least one filling tube (5, 6), which is disposed in the seam of the outer border zone (2, 3).

11. The multichamber bag according to claim 7, characterized in that the outer wall in the chamber separation zone is provided with at least one tear tab (10).

12. The multichamber bag according to claim 8, characterized in that in addition to the discharge tube (4) each chamber to be filled also has at least one filling tube (5, 6), which is disposed in the seam of the outer border zone (2, 3).

13. The multichamber bag according to claim 9, characterized in that in addition to the discharge tube (4) each chamber to be filled also has at least one filling tube (5, 6), which is disposed in the seam of the outer border zone (2, 3).

14. A method for preparing a mixed solution for dialysis, infusion, or nutrition, characterized by separating a seam between at least two chambers (8 and 9) of a multichamber medical bag of claim 7.

* * * * *

(12) EX PARTE REEXAMINATION CERTIFICATE (7022nd)
United States Patent
Kreischer et al.

(10) Number: US 6,017,598 C1
(45) Certificate Issued: Aug. 25, 2009

(54) MULTILAYER POLYMER FILM FOR A MULTICHAMBER MEDICAL BAG AND PROCESS FOR FABRICATION THEREOF

(75) Inventors: Thomas Kreischer, Saarbrucken (DE); Klaus Heilmann, St. Wendel (DE); Thomas Nicola, Forbach (DE); Michael Zimmermann, St. Wendel (DE)

(73) Assignee: Fresenius AG, Bad Homburg (DE)

Reexamination Request:
No. 90/008,897, Oct. 23, 2007

Reexamination Certificate for:
Patent No.: 6,017,598
Issued: Jan. 25, 2000
Appl. No.: 08/564,134
Filed: May 28, 1996

(22) PCT Filed: Mar. 28, 1995
(86) PCT No.: PCT/EP95/01152
§ 371 (c)(1), (2), (4) Date: May 28, 1996
(87) PCT Pub. No.: WO95/26177
PCT Pub. Date: Oct. 5, 1995

(30) Foreign Application Priority Data

Mar. 29, 1994 (DE) .............................. 4410876

(51) Int. Cl.
*A61J 1/10* (2006.01)
*B32B 7/06* (2006.01)

(52) U.S. Cl. ............ 428/35.4; 428/35.2; 428/35.7; 428/36.6; 428/43; 428/500; 428/516; 604/410; 604/416; 206/219; 206/828; 383/38; 383/200; 383/207; 156/306.3

(58) Field of Classification Search .................. None
See application file for complete search history.

(56) References Cited

U.S. PATENT DOCUMENTS

| | | |
|---|---|---|
| 3,211,144 A | 10/1965 | Nehring |
| 3,847,461 A | 11/1974 | Moeckl |
| 4,365,629 A | 12/1982 | Pert et al. |
| 4,479,989 A | 10/1984 | Mahai |
| 4,490,420 A | 12/1984 | Yoshida |
| 4,496,046 A | 1/1985 | Stone et al. |
| 4,519,499 A | 5/1985 | Stone et al. |
| 4,643,928 A | 2/1987 | Kimura et al. |
| 4,645,482 A | 2/1987 | Yoshida |
| 4,770,295 A | 9/1988 | Carveth et al. |

(Continued)

FOREIGN PATENT DOCUMENTS

| | | |
|---|---|---|
| CA | 2118900 | 9/1994 |
| CA | 2163022 | 10/1995 |
| DE | 3700713 | 7/1988 |
| DE | 3919360 | 12/1990 |
| DE | 4410876 | 10/1995 |

(Continued)

OTHER PUBLICATIONS

S. Canevarolo et al., "Preferential Plasticization of SBS Triblock Copolymer", *British Polymer Journal* (vol. 22–2, 137–141, 1989).
Shell Chemical Company product brochure: "*Kraton® Thermoplastic Rubber—Typical Properties*" (1988).

*Primary Examiner*—Terrence R Till (57) ABSTRACT

The invention concerns a multilayer polymer film and a multichamber bag, whose bag chambers are formed by seams in the outer border zone and by at least one seam in the chamber separation zone, whereby the seams are formed from the polymer materials facing the chambers. The polymer materials facing the chambers are inseparably sealed together in the outer border zone and sealed together in the chamber separation zone such that the seam is separable with a force which lies in the range from 5 to 20 N. The different strength of the bond from the sealing process is obtained by varying sealing temperatures.

U.S. PATENT DOCUMENTS

| | | | |
|---|---|---|---|
| 4,790,815 | A | 12/1988 | Balteau et al. |
| 4,803,102 | A | 2/1989 | Raniere et al. |
| 4,961,495 | A | 10/1990 | Yoshida et al. |
| 4,966,795 | A | 10/1990 | Genske et al. |
| 4,997,083 | A | 3/1991 | Loretti et al. |
| 5,143,535 | A | 9/1992 | Herrington et al. |
| 5,176,634 | A | 1/1993 | Smith et al. |
| 5,431,496 | A | 7/1995 | Balteau et al. |
| 5,520,972 | A | 5/1996 | Ezaki et al. |
| 5,577,369 | A | 11/1996 | Becker et al. |
| 6,017,598 | A | 1/2000 | Kreischer et al. |

FOREIGN PATENT DOCUMENTS

| | | |
|---|---|---|
| DE | 4447626 | 10/2001 |
| EP | 114964 | 8/1984 |
| EP | 196727 | 10/1986 |
| EP | 345774 | 12/1989 |
| EP | 0 345 774 A1 | 12/1989 |
| EP | 228819 | 1/1990 |
| EP | 380145 | 8/1990 |
| EP | 230114 | 12/1990 |
| EP | 0 437 856 A2 | 7/1991 |
| EP | 437856 | 7/1991 |
| EP | 513364 | 11/1992 |
| EP | 619998 | 10/1994 |
| EP | 635254 | 1/1995 |
| EP | 1264588 | 8/2004 |
| JP | 62-149441 | 7/1987 |
| JP | 63-317481 | 12/1988 |
| JP | 02-004671 | 1/1990 |
| JP | 02-057584 | 2/1990 |
| JP | 02-255148 | 10/1990 |
| JP | 03-067625 | 3/1991 |
| JP | 04-030853 | 2/1992 |
| JP | 04-292170 | 10/1992 |
| JP | 04-364850 | 12/1992 |
| JP | 05-293160 | 11/1993 |
| JP | 05-317385 | 12/1993 |
| JP | 07-051342 | 2/1995 |
| JP | 07-136234 | 5/1995 |
| JP | 08-511216 | 11/1996 |
| JP | 10-005309 | 1/1998 |
| WO | 8501268 | 3/1985 |
| WO | 8806897 | 9/1988 |
| WO | 9202271 | 2/1992 |
| WO | 9302016 | 2/1993 |
| WO | 9317863 | 9/1993 |
| WO | 9416664 | 8/1994 |
| WO | 9417772 | 8/1994 |

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 5, lines 10–14:

For easier handling, the seam 7 has on its outside two tear tabs [10]*11*.

Moreover, the seam 2, which is opposite the seam 3, which has the discharge tube, is outfitted with a suspension arrangement [11] *12* in the form of an opening.

Column 5, lines 37–43:

The structure of the film is described in detail in the three following examples with reference to 3-layer films which represent a preferred embodiment. In the examples, the outer layer of the film, which is the side facing away from the chambered bag, is referred to as *the first* layer [1]. [Layer 2] *The second layer* is the middle film and *the third* layer [3] is the side of the film facing the chambers.

Column 5, lines 52–65:

| | Film structure: | | | |
|---|---|---|---|---|
| | Plastic Type | Name | Manufacturer | MFI |
| *First Layer* [Layer 1] | 100% PP homopolymer | [Novolen] *NOVOLEN ®* 1302H | BASF | 1.8 (230/ 2.16) |
| *Second Layer* [Layer 2] | 70% VLDPE | [Teamex] *TEAMEX ®* 100F | DSM | 3.0 (190/ 2.16) |
| | 30% PP homopolymer | [Novolen] *NOVOLEN ®* 1302H | BASF | 1.8 (230/ 2.16) |
| *Third Layer* [Layer 3] | 70% PP random copolymer | [Novolen] *NOVOLEN ®* 3200HX | BASF | 1.8 (230/ 2.16) |
| | 30% SEBS compound | 90% [Kraton] *KRATON ®* G1650 | Shell | |
| | | 10% [Ondina] *ONDINA ®* G100 | Shell | |

Column 6, lines 3–12:

[Like] *Example 2 is like* Example 1, except that in [Layer 3] *the third layer* a commercially available product of the company GW-Kraiburg was used as an SEBS compound.

| | Plastic Type | Name | Manufacturer | MFI |
|---|---|---|---|---|
| *Third Layer* [Layer 3] | 70% PP-R | [Novolen] *NOVOLEN ®* 3200HX | BASF | 1.8 (230/ 2.16) |
| | 30% SEBS compound | TF6AAF | GW-Kraiburg | |

Column 6, lines 49–53:

The seams of the multichamber bag sealed at different pressures and in the temperature range from 115° C. to 131° C. were subjected to a tensile strength test according to DIN 53457. The results of this tensile strength test are graphically presented in FIG. 3 [and 4].

Column 7, lines 8–20:

For the film tested, the following temperature ranges result:

A seam which was sealed below [115° C.] *123° C.* can be separated with a force of less than 5 N/mm², i.e., the bond of the sealing surface is too low to be able to be used as seam in a multichamber bag according to the invention.

A seam which was sealed in the temperature range from [115° C. to 128° C.] *123° C. to 128° C.* can be separated with a force in the range from 5 N/mm² to 20 N/mm², i.e., such a seam is used according to the invention in the chamber separation zone, since this bond can subsequently be separated.

Column 7, lines 26–37:

FIG. 4a depicts a 3-layer film 15 structured according to Example 1 with inner layers 16 and 16' and with middle layers 17 and 17' as well as outer layers 18 and 18' which were sealed at a temperature higher than 128° C. The two inner layers 16 and 16', as can be seen in the graphic, are fused to each other such that *the matrix polymer regions 19 and 20 of the inner layers fuse, and* an inseparable bond is formed.

FIG. 4b depicts a 3-layer film 15 structured according to Example 1, as was described in FIG. 4a. The difference from FIG. 4a consists only in that the film was sealed in the temperature range from 123° C. to 128° C. In this case, the two inner layers 16 and 16', as can be seen in the graphic, are fused to each other such that *the matrix polymer regions 19 and 20 of the inner layers do not fuse, and* a subsequently separable bond is formed.

AS A RESULT OF REEXAMINATION, IT HAS BEEN DETERMINED THAT:

Claims 1–14 are cancelled.

New claims 15–28 are added and determined to be patentable.

*15. A method of sealing a multilayer polymer film including two or more layers, which, at a first sealing temperature, forms a peelable bond and, at a second higher sealing temperature, forms a permanent bond, wherein the sealing layer has a matrix phase polymer system, wherein the matrix polymer is a polyethylene homopolymer, a polyethylene copolymer, a polypropylene homopolymer, or a polypropylene copolymer and the phase polymer is a styrene ethylene/butylene styrene triblock polymer with a styrene ethylene/butylene diblock component, and/or a styrene ethylene/propylene styrene triblock polymer, which method comprises forming a seam which can be separated by a force in the range of 5 to 20 N/mm² by sealing the film at a temperature in the range of from 123° C. to 128° C.*

*16. The method according to claim 15, characterized in that the multilayer film is a co-extruded multilayer film.*

*17. The method according to claim 15, characterized in that the multilayer film has two to seven layers.*

*18. The method according to claim 15, characterized in that the phase polymer contains a processing aid.*

19. The method according to claim 15, characterized in that the proportion of the phase polymer is in the range from 1 to 40 wt. %, based on the matrix-phase polymer system.

20. The method according to claim 15, characterized in that the multilayer film has a gas barrier for oxygen and carbon dioxide as well as a water vapor barrier layer.

21. A multichamber medical bag (1) made of a polymer material for preparation of medical mixed solutions, which has at least two chambers (8 and 9), which are separated from each other by a sealed separation zone (7) to be opened and are sealed in an outer border zone (2, 3), whereby in the seam of the outer border zone at least one tube (4) is provided in at least one chamber, characterized in that it is fabricated from a multilayer polymer film including two or more layers, which, at a first sealing temperature, forms a peelable bond and, at a second higher sealing temperature, forms a permanent bond, wherein the sealing layer has a matrix phase polymer system, wherein the matrix polymer is a polyethylene homopolymer, a polyethylene copolymer, a polypropylene homopolymer, or a polypropylene copolymer and the phase polymer is a styrene ethylene/butylene styrene triblock polymer with a styrene ethylene/butylene diblock component, and/or a styrene ethylene/propylene styrene triblock polymer.

22. The multichamber bag according to claim 21, characterized in that the seam is separable in the separation zone (7) with a force which is in the range from 5 to 20 N/mm2 and the seam in the outer border zone (2, 3) is inseparable.

23. The multichamber bag according to claim 21, characterized in that it is heat sterilizable.

24. The multichamber bag according to claim 21, characterized in that in addition to the discharge tube (4) each chamber to be filled also has at least one filling tube (5, 6), which is disposed in the seam of the outer border zone (2, 3).

25. The multichamber bag according to claim 21, characterized in that the outer wall in the chamber separation zone is provided with at least one tear tab (11).

26. The multichamber bag according to claim 21, characterized in that in addition to the discharge tube (4) each chamber to be filled also has at least one filling tube (5, 6), which is disposed in the seam of the outer border zone (2, 3).

27. The multichamber bag according to claim 23, characterized in that in addition to the discharge tube (4) each chamber to be filled also has at least one filling tube (5, 6), which is disposed in the seam of the outer border zone (2, 3).

28. A method for preparing a mixed solution for dialysis, infusion, or nutrition, characterized by separating a seam between at least two chambers (8 and 9) of a multichamber medical bag of claim 21.

\* \* \* \* \*